United States Patent [19]

Filer

[11] Patent Number: 4,997,448
[45] Date of Patent: Mar. 5, 1991

[54] PROXIMAL CEMENT SEALING PLUG FOR HIP PROSTHESIS

[76] Inventor: Frederic C. Filer, 10 Mesa La., Colorado Springs, Colo. 80906

[21] Appl. No.: 310,305

[22] Filed: Feb. 13, 1989

[51] Int. Cl.⁵ .............................................. A61F 2/36
[52] U.S. Cl. ...................................... 623/23; 623/16; 606/92; 606/95
[58] Field of Search ....................... 623/23, 16; 606/92, 606/93, 94, 95

[56] References Cited

U.S. PATENT DOCUMENTS

| 4,245,359 | 1/1981 | Stuhmer | 623/16 |
| 4,523,587 | 6/1985 | Frey | 606/95 |
| 4,783,192 | 11/1988 | Wroblewski et al. | 623/23 |

FOREIGN PATENT DOCUMENTS 2425237 12/1979 France .

Primary Examiner—Randall L. Green
Assistant Examiner—Stephanie L. Iantorno
Attorney, Agent, or Firm—Richard W. Hanes

[57] ABSTRACT

The present invention relates to method and apparatus for implanting and cementing the femoral stem component of a hip prosthesis. The process includes the steps of resecting the femoral neck, reaming a bore into the proximal medullary canal, enlarging that bore to accommodate the elongated stem of the femoral component, including the greater enlargement of the portion of the bore adjacent the transverse plane of the neck resection, establishing a peripheral shoulder in the cancellous bone of the medullary canal to seat a sealing plug, installing on the seat a perforable sealing plug, injecting the cavity with cement and implanting the femoral stem in the enlarged bore of the medullary canal by puncturing the sealing plug with the distal end of the stem and moving the stem distally further so that the sealing plug becomes a collar around the stem intermediate its ends. The apparatus of the invention comprises a pliant sealing plug adapted and sized to fit tightly into the broached bore of the medullary canal and which has a perforable center section to allow the stem to puncture the plug and be implanted in the medullary canal by introducing it through the sealing cavity above the plug. Having sealed off the distal portion of the bore, no cement is allowed to intrude into the area below the seal, preventing the lower portion of the femoral stem from being cemented in the bone.

4 Claims, 3 Drawing Sheets

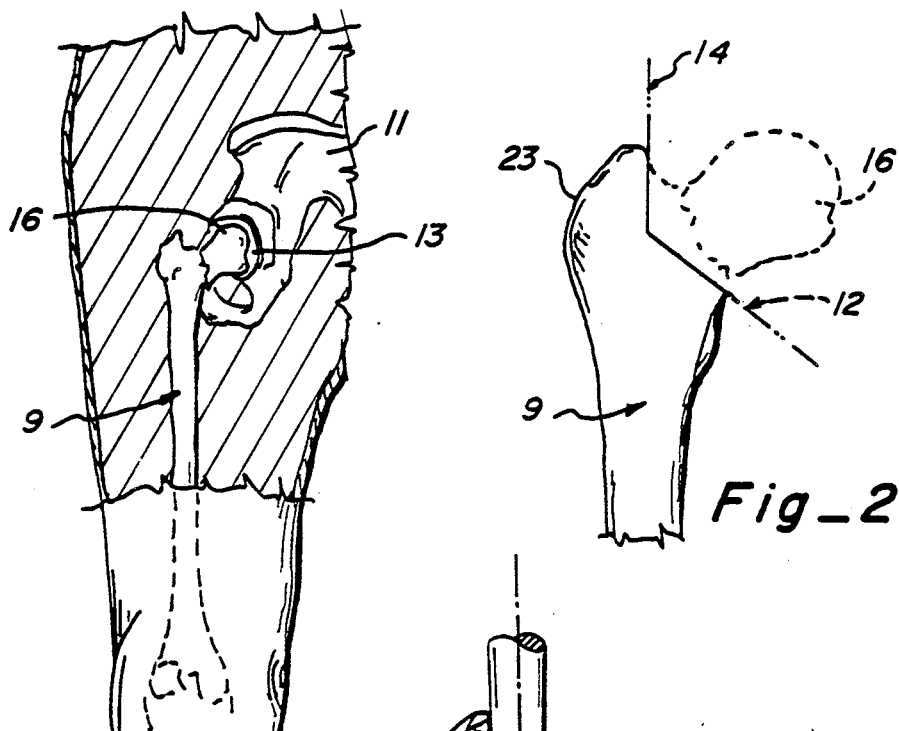
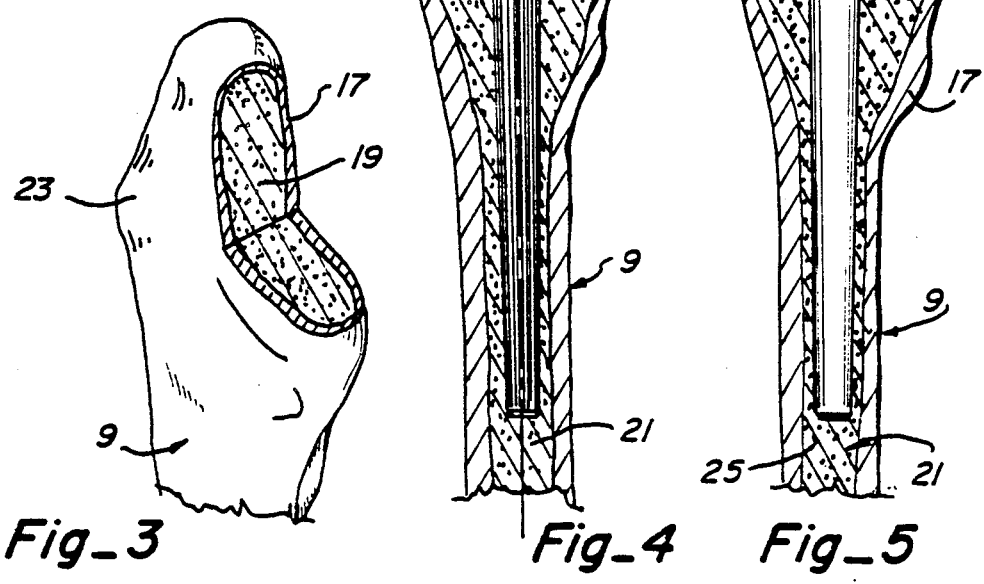

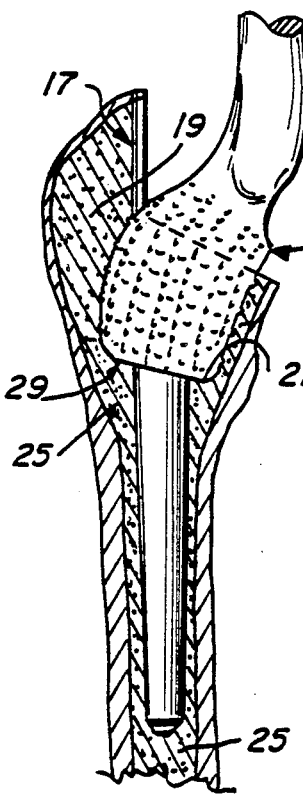
Fig_6
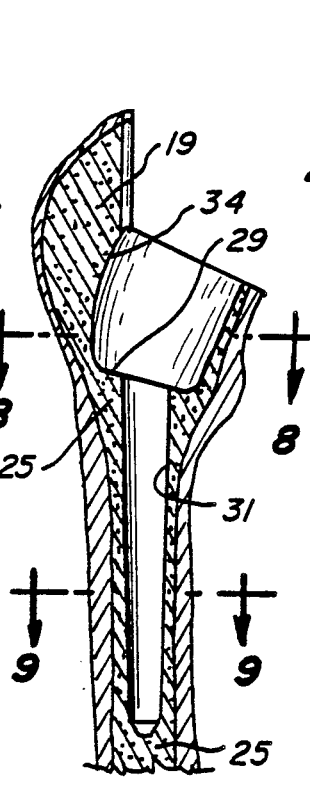
Fig_7
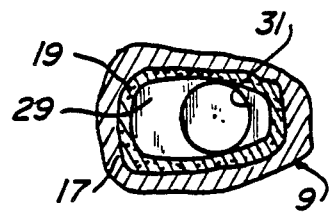
Fig_8
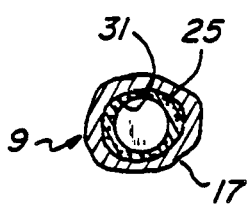
Fig_9
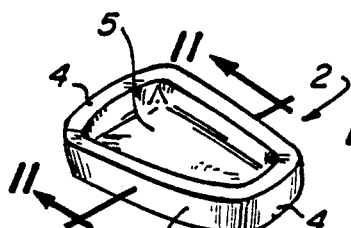
Fig_10
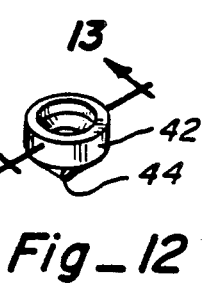
Fig_12
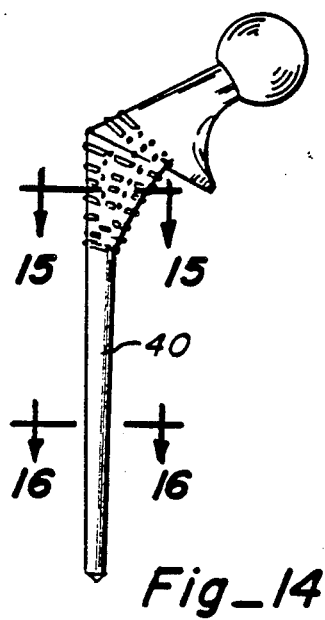
Fig_14
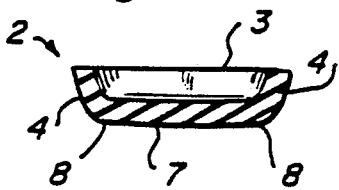
Fig_11
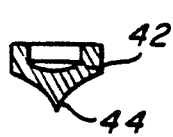
Fig_13

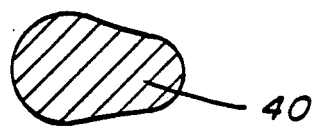
Fig_15
Fig_16
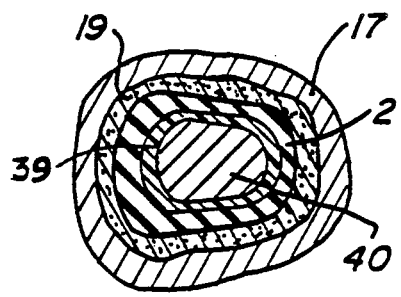
Fig_18
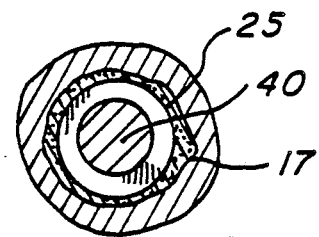
Fig_19
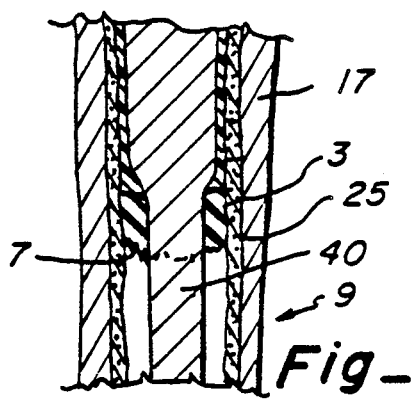
Fig_20
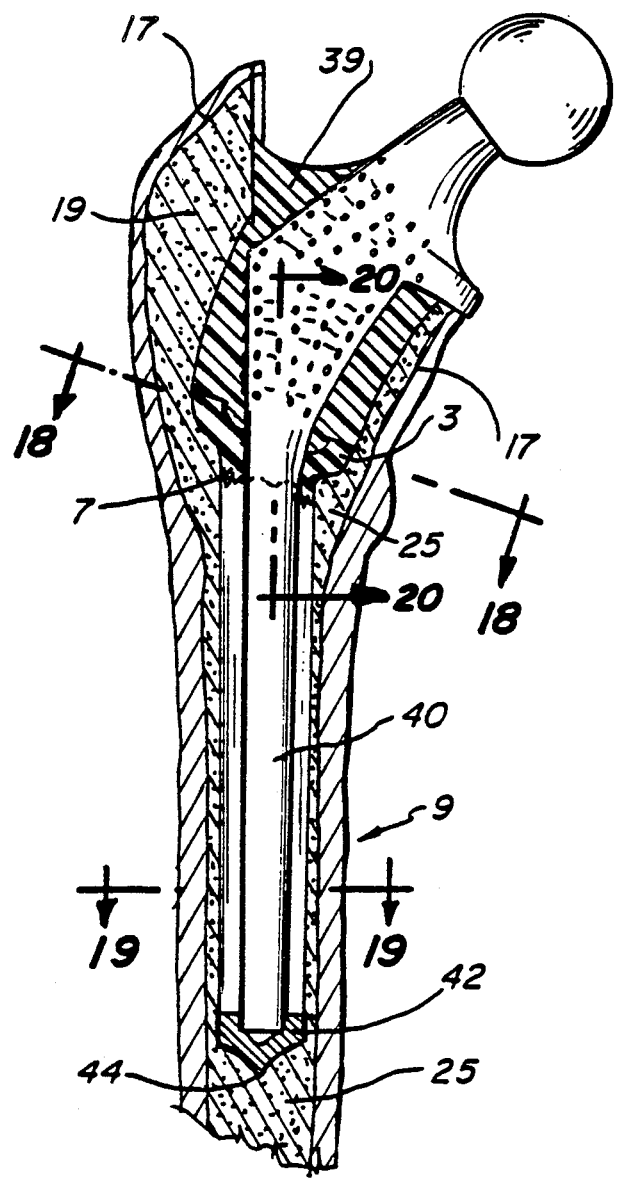
Fig_17

PROXIMAL CEMENT SEALING PLUG FOR HIP PROSTHESIS

FIELD OF THE INVENTION

The present invention relates to hip prostheses and the method of implanting and cementing the femoral stem into place. More specifically, the invention concerns a proximal cement blocking or sealing plug which is placed in the metaphysis of the femur in the medullary canal to prevent the cement from embracing the lower portion of the stem of the prosthesis.

BACKGROUND OF THE INVENTION

Hip prostheses, or artificial hips as they are sometimes known, have been in existence for many years, long enough to have accumulated a track record evidencing the strengths and weaknesses of the systems and their methods of implantation. In a total hip system, these prosthetic joints each consist of a substantially hemispherical acetabular cup adapted to be fixed into the acetabulum of the pelvis and a mating metallic ball which is carried by the proximal end of a long rigid femoral stem imbedded in the medullary canal of the proximal femur. Roughly sixty percent of these femoral stems are fixed in place by cement.

The number one complication of cemented total hip replacements is post-operative loosening of the components. Not only is this the most common complication, it rapidly increases with time, and in certain instances can be among the most severe complications following this kind of surgery. As an example of this severity, an increasing number of patients require a girdlestone procedure because of the severity of the failure and the massive bone destruction secondary to non-septic component loosening. Research figures indicate a 4% incidence of x-ray evidence of loose femoral components after two years. The same group of patients, when followed four to seven years later, evidenced a failure of cement fixation of up to 24%. Of special note was the incidence of 50% loose femoral components in one subset, those patients who had a small femoral component in a large canal.

Other figures show the failure on the femoral side of the prosthesis was 19.5% in cases followed three years post-operatively and this rose in a five to seven -year post-operative period to 42%. With the passage of time, the number of patients disabled with pain secondary to this loosening also rises, leading to a progressively increasing clinical failure rate.

The adequate securing of the acetabular component within the acetabulum has been the thrust of much research and development, but is not the subject of this invention and will not be discussed herein.

While a number of alternatives have been proposed to replace conventional cementing, none have yet proven to be a satisfactory solution. Better cements have not solved the problem nor is bony ingrowth sufficiently established to be widely adopted as an alternative in all cases. The surface replacement operation avoids the need to cement in a femoral stem, but the rapidly rising rate of early failure of surface replacement units makes the use of this approach limited.

For most surgeons, the optimum solution to this dilemma of loosening is to try to improve the traditional cementing techniques with such concepts as obtaining better fixation by virtue of improved intrusion of the cement into the trebecular bone by confining the cement in a specified space while increasing the intrusion pressure. To accomplish these ends, cement guns and compactor apparatus have been introduced, as well as the method of inserting a medullary plug at the base or distal end of the femoral stem, prior to cement injection, to restrict the flow of the cement to the space around the length of the stem. Yet another method sought to improve the cement fixation of the components is to centrifuge the cement prior to injection to expel entrained air bubbles.

In accordance with these state of the art methods and objectives, the stems are encased over their entire length in cement in order to provide a surrounding fixation casement between the stem and the femoral bone. Eliminating voids and bubbles in the cement maximizes the strength of the cement by adding to its homogeneity. Elaborate surfaces and metal finishes for the stem have also been designed to encourage bonding between the cement and the metal stem and, as mentioned earlier, the cement itself has undergone improvement to increase its penetration of the interstices of the trabecular bone.

Notwithstanding these efforts, however, loosening of the stem is a continuing problem after the prosthesis has been in place for a number of years, requiring revision surgery or other methods to alleviate the patient's pain and disability.

The most common area of failure and loosening of the femoral stem is in the proximal femur. While the cement fills the space between the metal stem of the prosthesis and the bone at the time of implantation, and in most case creates a satisfactory fixation, after time the bone itself becomes subject to osteoporosis and thinning which is followed by fracture of the cement mantle surrounding the stem, allowing the stem to toggle about its lower end as a pivot point. The cause of the osteoporosis is significant to the present invention. Bone, like living muscle tissue, develops and remains strong and healthy with use. In the case of bones like the femur, the accommodation of stress keeps the bone structure healthy.

Until this invention, it has been thought necessary to cement the entire length of the femoral stem to insure its adequate stability for the long femoral stem. When that is done, however, the compressive and other stresses created in and through the stem when the leg is used are transferred to the femoral bone near the distal end of the prosthetic stem, not uniformly along its length. The fixation created between the cement and the portion of the bone surrounding the lower portion of the stem transfers the forces developed through the ball joint to the lower portion of the femur and by-passes its proximal end —that is, there is stress shielding of the proximal femoral bone. Over a period of time, that portion of the bone which is stress-shielded is subject to the deterioration of osteoporosis and begins to atrophy and thin; the cement mantle proximally fractures, usually radially of the stem, allowing the cement mantle to spread open, bringing on unacceptable toggle movement of the stem within the bone. It has been discovered as a fundamental part of this invention that cementing the entire length of the femoral stem is not only unnecessary, but is counter-productive to the objective of maintaining fixation of the stem within the femur over long periods of time. It is further apparent through the teaching of this invention that cementing only the proximal portion of the femoral stem, from the lower metaphysis to the plane of the transverse cut of the femoral neck osteotomy, will eliminate osteoporosis of the bone by transferring the stresses to the proximal femur and not shielding them therefrom.

It is therefore the principle object of the present invention to provide an apparatus and method for restricting the length of the cement mantle surrounding the femoral prosthesis stem so that the lower end of the stem will not be cemented, thereby creating a system for transferring the dynamic forces generated in the upper portion of the stem to the proximal femur and thus eliminating stress shielding of the proximal femur and the consequent deterioration of the bone in that area.

Within that overall objective, it is a further objective of the invention to provide a plug which is inserted in the specially prepared medullary canal, prior to the injection of the cement, which will prevent the flow of cement past the plug toward the distal end of the femoral stem.

A still further object of the invention is to provide a novel method of implanting a femoral stem which eliminates the need for large quantities of cement which, in a large-boned person, may require, under state of the art techniques, a refilling of the cement gun during a time-critical portion of the surgery.

Other and further objects, features and advantages of the invention will become apparent from a reading of the detailed description of the invention which follows.

THE PRIOR ART

The most pertinent prior art known resides in the current procedures for hip replacement currently used by practicing orthopedic surgeons. As briefly referred to above, one of these practices involves the use of a medullary cement restricting plug which is inserted in the medullary canal prior to cement injection. The plug is driven down the length of the canal to reside at a position distal to the final position of the end of the femoral stem. The purpose of such a plug is to provide a stop for the cement so that it will not continue into the depth of the canal as it is injected under pressure. With such backstop, the voids in the cement are filled, creating a homogeneous mass in the area into which the femoral stem will be inserted. The use of such a device, by definition, contemplates cementing the entire length of the stem component and since the medullary plug is inserted to a depth which will be below the tip of the femoral stem there is never the necessity for any contact between the stem and the plug during the implantation process.

DESCRIPTION OF THE DRAWINGS

FIG. 1 is an anterior fragmented view of a human right leg with portions thereof broken away and shown in cross-section.

FIG. 2 is a fragmentary view of the proximal femur showing the neck and head thereof in dashed lines, representing the portion of the femur resected in order to implant an artificial hip prosthesis.

FIG. 3 is a fragmentary perspective view of the proximal femur after the resection of the femoral neck.

FIG. 4 is a fragmentary cross-sectional view of the proximal femur illustrating a reaming tool in place in the medullary canal.

FIG. 5 is a cross-sectional view similar to that of FIG. 4 showing the bore in the medullary canal following the reaming process.

FIG. 6 is a cross-sectional view similar to FIG. 5 but illustrating a broaching tool in place to proximally enlarge the bore shown in FIG. 5.

FIG. 7 is a cross-sectional view similar to that of FIG. 6 showing the enlarged cavity in the medullary canal following the broaching process.

FIG. 8 is a cross-sectional view taken along lines 8—8 in FIG. 7.

FIG. 9 is a cross-sectional view taken along lines 9—9 in FIG. 7.

FIG. 10 is a perspective view of the proximal cement sealing plug of the present invention.

FIG. 11 is a cross-sectional view taken along lines 11—11 of FIG. 10.

FIG. 12 is a perspective view of the centralizer cup which attaches to the distal end of the stem of the femoral prosthesis.

FIG. 13 is a cross-sectional view taken along lines 13—13 of FIG. 12.

FIG. 14 is a side elevational view of a typical prosthetic femoral stem.

FIG. 15 is a cross-sectional view taken along lines 15—15 of FIG. 14.

FIG. 16 is a cross-sectional view taken along lines 16—16 in FIG. 14.

FIG. 17 is a fragmentary cross-sectional view of the proximal femur showing the prosthetic femoral stem implanted.

FIG. 18 is a cross-sectional view taken along lines 18—18 of FIG. 17.

FIG. 19 is a cross-sectional view taken along lines 19—19 of FIG. 17.

FIG. 20 is a fragmentary cross-sectional view taken along lines 20—20 in FIG. 17.

DETAILED DESCRIPTION

The apparatus of the invention is seen in FIGS. 10 and 11 and is identified generally by reference numeral 2. The choices of plan view shape and dimensions of the medullary cement sealing plug will be explained in more detail in connection with the description of the procedure in which the plug is used, which follows. The plug may be constructed of a flexible material such as a silicone elastomer, polyethylene, a body-absorbable substance or the like. Generally, the sealing plug comprises a body 3 having inclined side walls 4 defining an open central area 5 and whose bottom comprises a thin perforable membrane 7 which is impervious to the cement used to fix the femoral stem. The plan view of the sealing plug in FIG. 10 is substantially trapezoidal, but is variable in its design, conforming substantially to the cross-sectional footprint of the femoral stem 40 at the level of the distal end of the metaphysis of the femur. Further details of the plug 2 will be better explained and understood in connection with a description of the process of implanting the femoral stem, using the method and apparatus of the present invention.

Arthritic and fractured hips which show poor promise of healing present frequent candidates for an artificial hip. A diagrammatic representation of a human femur 9 fractured through the femoral neck is seen in FIG. 1 where a portion of the pelvic bone 11 and the acetabulum 13 are illustrated.

After opening and with the head of the femur 16 properly presented, the first step in the implant procedure is the femoral neck osteotomy. A transverse cut is completed along a line defined by the plane 12 in FIG. 2 and a sagittal cut is made along the plane 14 to free the head 16 for removal, presenting the proximal femur as seen in FIG. 3. The cortical bone 17 and the porous trabecular bone 19 are seen after resection of the neck and head.

A first axial reamer 20 having a trocar point is inserted in the postero-lateral portion of the resected surface of the femoral neck and as it enters the medullary canal 21 the reamer is pushed laterally against the greater trochanter 23. The side cutting flutes of the reamer allow the reamer to align itself within the medullary canal. Successively greater diameter reamers are used until the reamer begins to bind in the femoral isthmus, indicating that the reaming procedure is complete.

Next, proximal shaping for the femoral stem is accomplished with a broach 26 following the bore 24 created by the reamer 20. Contrary to the design of traditional broaches made for this purpose, the broach 26 is provided with an annular shoulder 27 intermediate its ends, which shoulder defines the lower extent of the broach teeth, as seen in FIG. 6. The shoulder, having rounded edges, forms a corresponding seat or abutment 29 around the perimeter of the cancellous bone 25 in the medullary canal 21.

Following the broaching step done with the broach 26, the plug 2 is inserted into the enlarged opening 34 with the membrane 7 distally oriented. The flange 8, formed by that portion of the lower surface of the sealing plug body which lies beneath its upstanding stiffening walls, is positioned on the seat 29 which was broached in the cancellous bone 25, forming a sealing partition between the proximal enlarged cavity 34 and the more distal bore 31.

Cement 39 is injected with an appropriate pressure device to fill the cavity 34, followed by insertion of the femoral stem 40. An annular centralizer 42, seen in FIGS. 12 and 13 may be mounted on the distal end of the stem 40. The centralizer is provided with a sharply pointed underside 44 for the purpose of puncturing the membrane 7 of the plug 2 as the stem is inserted down into its final position in the medullary canal, as depicted in FIG. 17. If the femoral stem is not tapered below the level of the sealing plug, as it need not be when it is not cemented along this portion of its length, then the diameter of the bore 31 need be large enough only to accommodate the stem and, in such case, the prosthetic stem itself may be pointed or otherwise modified to perforate the membrane 7 of the sealing plug 2 when the stem is inserted down into the medullary canal.

Femoral stems are constructed of many different cross sections and with a number of different dimensions to accommodate various bone sizes. The plugs 2 are shaped to imitate the cross-section of the femoral stem and are sized to fit snugly into the cavity 34 so as to present an impervious barrier to the pressurized cement 39 when it is injected.

Thus, it is seen that if the proximal sealing plug of the present invention is inserted and used as generally discussed above the viscous cement will not proceed distally past the plug 2, leaving the distal portion of the femoral stem uncemented, but stabilized, either with the centralizer 42 or by close fit of the stem in the medullary canal. Elimination of the stress shielding of the proximal femur will have been accomplished with a minimum of disruption to the procedure which is common to hip replacement technology.

What is claimed is:

1. A prosthesis implant assembly comprising:
   an elongated rigid stem having proximal and distal end portions;
   a head carrying neck disposed angularly thereto and attached to the proximal end portion of the stem; and
   pliant oblong means for sealing cement around said proximal end portion of said stem, said means having proximal and distal surfaces and a closed bottom wall which can be perforated in vivo by the stem.

2. A prosthesis implant assembly comprising:
   an elongated rigid stem having proximal and distal end portions;
   a head carrying neck attached to the proximal end portion of the stem;
   pliant oblong sealing means having a closed bottom wall which can be perforated in vivo by the stem; and
   means on said distal end portion of said stem for perforating said wall of said sealing means.

3. A prosthesis implant assembly comprising:
   an elongated rigid stem having proximal and distal end portions;
   a head carrying neck disposed angularly thereto and attached to the proximal end portion of the stem;
   pliant oblong means having proximal and distal surfaces and a perforated center section carried annularly by the stem intermediate its said end portions; and
   annular centralizer means carried by the distal end of the said stem and wherein said centralizer means includes a sharp projecting distal point for perforating the center section of the sealing means.

4. The prosthesis of claim 3 wherein the centralizer means comprises a cup shaped body in which the distal end of the stem is disposed.

* * * * *

UNITED STATES PATENT AND TRADEMARK OFFICE
CERTIFICATE OF CORRECTION

PATENT NO. : 4,997,448

DATED : Mar. 5, 1991

INVENTOR(S) : Frederic C. Feiler

It is certified that error appears in the above-identified patent and that said Letters Patent is hereby corrected as shown below:

On the title page, the inventor's last name, under item [19] and in item [76], "Filer" should be --Feiler--.

Signed and Sealed this

Fifteenth Day of October, 1991

Attest:

HARRY F. MANBECK, JR.

*Attesting Officer*     *Commissioner of Patents and Trademarks*